United States Patent
Moutai et al.

(10) Patent No.: US 11,578,132 B2
(45) Date of Patent: Feb. 14, 2023

(54) METHOD FOR PRODUCING B CELL POPULATION AND METHOD FOR PRODUCING MONOCLONAL ANTIBODY USING SAME

(71) Applicants: KANEKA CORPORATION, Osaka (JP); TOKYO UNIVERSITY OF SCIENCE FOUNDATION, Tokyo (JP)

(72) Inventors: Tatsuya Moutai, Hyogo (JP); Tomoyuki Nakaishi, Hyogo (JP); Hiroshi Kita, Hyogo (JP); Mitsuaki Kitano, Hyogo (JP); Daisuke Kitamura, Tokyo (JP)

(73) Assignees: KANEKA CORPORATION, Osaka (JP); TOKYO UNIVERSITY OF SCIENCE FOUNDATION, Tokyo (JP)

( * ) Notice: Subject to any disclaimer, the term of this patent is extended or adjusted under 35 U.S.C. 154(b) by 746 days.

(21) Appl. No.: 16/478,295

(22) PCT Filed: Jan. 15, 2018

(86) PCT No.: PCT/JP2018/000757
§ 371 (c)(1),
(2) Date: Sep. 12, 2019

(87) PCT Pub. No.: WO2018/131698
PCT Pub. Date: Jul. 19, 2018

(65) Prior Publication Data
US 2020/0071410 A1    Mar. 5, 2020

(30) Foreign Application Priority Data

Jan. 16, 2017 (JP) .............................. JP2017-004860

(51) Int. Cl.
*C12N 15/85* (2006.01)
*C07K 16/28* (2006.01)
*C12N 5/0781* (2010.01)
*A61K 39/00* (2006.01)

(52) U.S. Cl.
CPC ...... *C07K 16/2878* (2013.01); *A61K 39/0011* (2013.01); *C07K 16/2875* (2013.01); *C12N 5/0635* (2013.01); *C07K 2317/14* (2013.01); *C12N 2501/2302* (2013.01); *C12N 2501/232* (2013.01); *C12N 2501/2304* (2013.01); *C12N 2501/2312* (2013.01); *C12N 2501/2321* (2013.01); *C12N 2501/2324* (2013.01); *C12N 2501/2327* (2013.01); *C12N 2501/25* (2013.01); *C12N 2501/52* (2013.01)

(58) Field of Classification Search
None
See application file for complete search history.

(56) References Cited

U.S. PATENT DOCUMENTS

2012/0214192 A1    8/2012 Kitamura et al.

FOREIGN PATENT DOCUMENTS

| CN | 103946236 A | 7/2014 |
| EP | 2495312 A1 | 9/2012 |
| JP | 2011-092142 A | 5/2011 |
| JP | 2012029685 | * 1/2012 |
| JP | 2012-29685 A | 2/2012 |
| JP | 5550132 B2 | 7/2014 |
| WO | 200246233 A1 | 6/2002 |
| WO | 2016/002760 A1 | 1/2016 |

OTHER PUBLICATIONS

Notice of Reasons for Refusal issued in corresponding Japanese Application No. 2018-561437 dated Nov. 2, 2021 (8 pages).
R. J. Armitage et al., "Molecular and biological characterization of a murine ligand for CD40", Nature, May 7, 1992, vol. 357, pp. 80-82 (3 pages).
D. Hollenbaugh et al., "The human T cell antigen gp39, a member of the TNF gene family, is a ligand for the CD40 receptor: expression of a soluble form of gp39 with B cell co-stimulatory activity", The EMBO Journal, 1992, vol. 11, No. 12, pp. 4313-4312 (9 pages).
P. Schneider et al., "BAFF, a Novel Ligand of the Tumor Necrosis Factor Family, Stimulates B Cell Growth", J. Exp. Med., Jun. 7, 1999, vol. 189, No. 11, pp. 1747-1756 (10 pages).
P. A. Moore et al., "BLyS: Member of the Tumor Necrosis Factor Family and B Lymphocyte Stimulator", Science, Jul. 9, 1999, vol. 285, pp. 260-263 (5 pages).
A. Mukhopadhyay et al., "Identification and Characterization of a Novel Cytokine, THANK, a TNF Homologue That Activates Apoptosis, Nuclear Factor-kB, and c-Jun NH2-Terminal Kinase", J. Bio. Chem., 1999, vol. 274, No. 23, pp. 15978-15981 (5 pages).
G. Maarof et al., "Interleukin-24 inhibits the plasma cell differentiation program in human germinal center B cells", Blood, Mar. 4, 2010, vol. 115, No. 9, pp. 1718-1726 (10 pages).
F. Larousserie et al., "Differential Effects of IL-27 on Human B Cell Subsets", Journal of Immunology, 2006, vol. 176, No. 10, pp. 5890-5897 (9 pages).

(Continued)

*Primary Examiner* — Celine X Qian
(74) *Attorney, Agent, or Firm* — Osha Bergman Watanabe & Burton LLP

(57) ABSTRACT

It is an object of the present invention to provide a method for efficiently producing a B cell population comprising B cells that recognize a specific antigen. According to the present invention, provided is a method for producing a B cell population, comprising: a step (c) of culturing a cell population comprising B cells together with a specific antigen in the absence of IL-21, in the absence of IL-4, and in the presence of a cytokine other than IL-21 and IL-4, while giving stimulation mediated by CD40 and a BAFF receptor to the cells; and a step (d) of culturing the cell population comprising B cells, while giving stimulation mediated by has to the cells, so as to obtain a B cell population comprising B cells that recognize the specific antigen.

13 Claims, 2 Drawing Sheets

(56) References Cited

OTHER PUBLICATIONS

T. Suda et al., "Molecular Cloning and Expression of the Fas Ligand, a Novel Member of the Tumor Necrosis Factor Family", Cell, Dec. 17, 1993, vol. 75, pp. 1169-1178 (10 pages).
T. Moutai et al., "A Novel and Effective Cancer Immunotherapy Mouse Model Using Antigen-Specific B Cells Selected In Vitro", PLoS One, Mar. 2014, vol. 9, No. 3, e92732, pp. 1-10 (10 pages).
S. Yamaguchi et al., "Characterization of common marmoset dysgerminoma-like tumor induced by the lentiviral expression of reprogramming factors", Cancer Science, Apr. 2014, vol. 105, No. 4, pp. 402-408 (7 pages).
International Search Report issued in International Application No. PCT/JP2018/000757, dated Apr. 10, 2018 (4 pages).
Written Opinion issued in International Application No. PCT/JP2018/000757, dated Apr. 10, 2018 (7 pages).
International Preliminary Report on Patentability issued in International Application No. PCT/JP2018/000757, dated Jul. 25, 2019 (11 pages).
D. Kitamura, "Generation of B-cell memory from the in-vitro-induced germinal center B cells", Immunology, 2012, vol. 137, Suppl. 1, p. 332 (1 page).
C. A. K. Borrebaeck et al., "Human monoclonal antibodies produced by primary in vitro immunization of peripheral blood lymphocytes", Proceedings of the National Academy of Sciences USA, Jun. 1988, vol. 85, No. 11, pp. 3995-3999 (5 pages).
L. Moens et al., "Cytokine-mediated regulation of plasma cell generation: IL-21 takes center stage", Frontiers in Immunology, Jan. 2014, vol. 5, pp. 1-13 (13 pages).
T. Tamura et al., "Anti-Peptide Antibody Production Elicited by in Vitro Immunization of Human Peripheral Blood Mononuclear Cells", Bioscience, Biotechnology and Biochemistry, Dec. 7, 2007, vol. 71, No. 12, pp. 2871-2875 (6 pages).
Extended European Search Report issued in corresponding European Application No. 18738756.8, dated Jul. 27, 2020 (8 pages).
Office Action issued in corresponding European Patent Application No. 18738756.8 dated Mar. 31, 2021 (4 pages).
Office Action issued in corresponding Chinese Application No. 201880018239.8; dated Oct. 25, 2022 (16 pages).
Chinese Journal of Microbiology and Immunology, vol. 27, No. 7, Jul. 2007 (4 pages).

* cited by examiner

[Fig. 1]
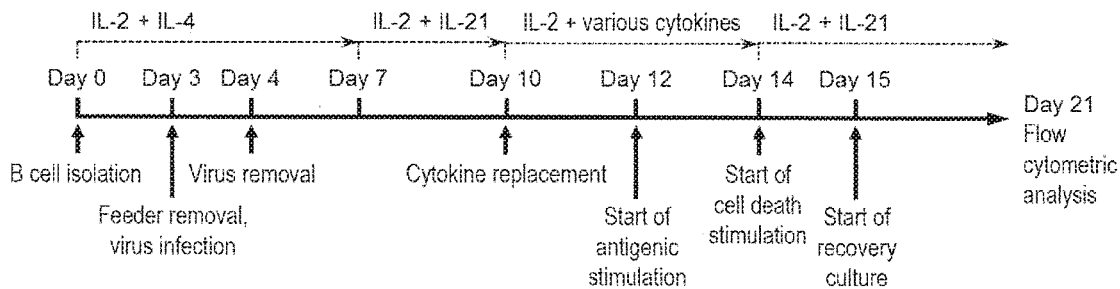
[Fig. 2]
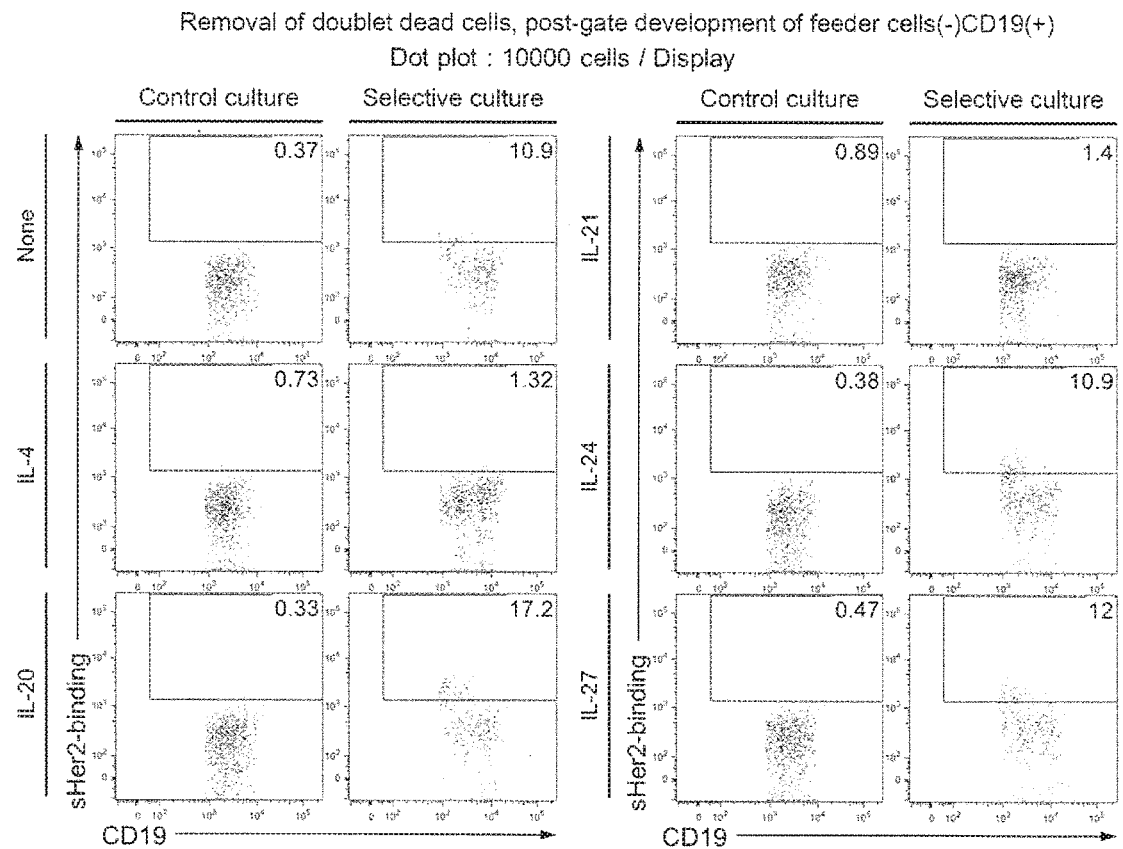

[Fig. 3]
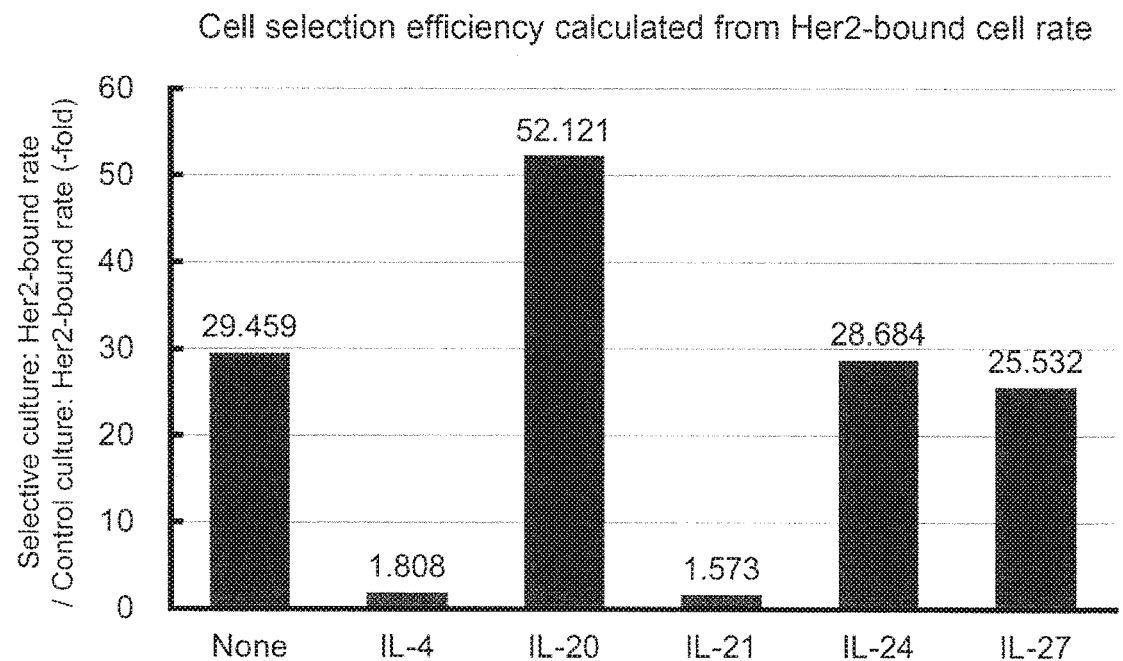

METHOD FOR PRODUCING B CELL POPULATION AND METHOD FOR PRODUCING MONOCLONAL ANTIBODY USING SAME

TECHNICAL FIELD

The present invention relates to a method for producing a B cell population, and a method for producing a monoclonal antibody using the same.

BACKGROUND ART

It is anticipated that a monoclonal antibody exhibiting high selectivity to a specific antigen will be developed as an antibody drug, and in particular, the development of antibody drugs targeting cancer cells has progressed. In order to apply a medicament comprising a monoclonal antibody as an active ingredient to the treatment for humans, administration of a human antibody comprising a small amount of foreign antigen is most ideal from the viewpoint of the avoidance of rejection. Hence, a large number of chimeric antibodies and humanized antibodies have been developed.

In general, chimeric antibodies or humanized antibodies used for the treatment of humans are produced by immunizing mice or other animals with antigens several times, then fusing cells of the spleen or lymph nodes with myeloma cells to form hybridomas, and then applying a recombination technique to mouse IgG antibodies produced from the hybridomas. However, it takes much time to use an individual animal such as a mouse or to select hybridomas that generate antibodies exhibiting a high affinity. Moreover, it is necessary to confirm the activity of an antibody obtained by a recombination technique. Thus, it takes time to produce an antibody of interest by the aforementioned method, and further, the effects of the produced antibody cannot be secured until it is administered to a human. Furthermore, when an immunogen exhibits individual toxicity, immunization to an individual is difficult. Further, when a protein antigen that is highly preserved among animal species is used as an antigen, an antibody is hardly generated due to immunological tolerance.

B cells are immune cells that are derived from bone marrow, have B cell receptors (BCR) on the surface thereof, and produce antibodies. Such B cells are generated from hematopoietic stem cells, and the cells are differentiated into B cells through the stage of pro-B cells and pre-B cells. It has been known that the B cells which produce antibodies exhibiting a high affinity for antigens are selected in a germinal center. However, this selection mechanism has not yet been elucidated. If such B cells which produce antibodies exhibiting a high affinity for specific antigens were allowed to artificially proliferate and could be then concentrated, monoclonal antibodies exhibiting a high affinity for specific antigens could be produced in a shorter time than previous techniques.

Patent Document 1 discloses a method for producing an antigen-specific B cell population comprising IgG-positive B cells specific to specific antigens, wherein the method comprises culturing IgG-positive B cells together with the specific antigens in the presence of IL-21, while giving stimulation mediated by CD40, a BAFF receptor and Fas to the cells, and then selecting antigen-specific B cells specific to the specific antigens from the cultured cells, so as to obtain an antigen-specific B cell population comprising IgG-positive B cells specific to the specific antigens.

Patent Document 2 discloses a method for producing a B cell population, comprising a step of culturing B cells in which the expression of a Bach2 gene is increased, in the presence of a means for acting on CD40 and/or a BAFF receptor.

PRIOR ART DOCUMENTS

Patent Documents

Patent Document 1: Japanese Patent No. 5550132
Patent Document 2: International Publication WO 2016/002760

SUMMARY OF INVENTION

Object to be Solved by the Invention

It is an object of the present invention to provide a method for efficiently producing a B cell population comprising B cells that recognize a specific antigen.

Means for Solving the Object

As a result of intensive studies in order to achieve the above object, the present inventors have found that a B cell population comprising B cells that recognize a specific antigen can be efficiently produced by culturing the cell population comprising B cells together with the specific antigen in the absence of IL-21, in the absence of IL-4, and in the presence of a cytokine other than IL-21 and IL-4, while giving stimulation mediated by CD40 and a BAFF receptor to the cells, and then by culturing the cell population comprising B cells, while giving stimulation mediated by Fas to the cells, thereby completing the present invention.

Specifically according to the present invention, the following inventions are provided.

[1] A method for producing a B cell population, comprising:
a step (c) of culturing a cell population comprising B cells together with a specific antigen in the absence of IL-21, in the absence of IL-4, and in the presence of a cytokine other than IL-21 and IL-4, while giving stimulation mediated by CD40 and a BAFF receptor to the cells; and
a step (d) of culturing the cell population comprising B cells, while giving stimulation mediated by Fas to the cells, so as to obtain a B cell population comprising B cells that recognize the specific antigen.
[2] The method according to [1], wherein the cytokine is an interleukin other than IL-21 and IL-4.
[3] The method according to [1] or [2], wherein the cytokine is at least one type of cytokine selected from IL-2, the IL-10 family and the IL-12 family.
[4] The method according to any one of [1] to [3], wherein the cytokine is at least one type selected from IL-2, IL-20, IL-24 and IL-27.
[5] The method according to any one of [1] to [4], wherein, in the step (d), the cell population comprising B cells is cultured in the presence of IL-21 or in the presence of IL-21 and IL-2, while giving stimulation mediated by Fas to the cells.
[6] The method according to any one of [1] to [5], wherein the step (d) is carried out in the absence of the specific antigen.
[7] The method according to any one of [1] to [6], which further comprises, before the step (c), a step (a) of culturing the cell population comprising B cells in the presence of IL-4 or in the presence of IL-4 and IL-2, while giving stimulation mediated by CD40 and a BAFF receptor to the cells.

[8] The method according to [7], which further comprises, between the step (a) and the step (c), a step (b) of culturing the cell population comprising B cells in the presence of IL-21 or in the presence of IL-21 and IL-2, while giving stimulation mediated by CD40 and a BAFF receptor to the cells.

[9] The method according to any one of [1] to [8], wherein the step (c) is a step of culturing the cell population comprising B cells, using a carrier that presents CD40L, BAFF and a specific antigen.

[10] The method according to wherein the carrier that presents CD40L, BAFF and a specific antigen is a feeder cell that presents CD40L, BAFF and a specific antigen.

[11] The method according to any one of [1] to [10], wherein the step (d) is a step of culturing the cell population comprising B cells, using a carrier that presents CD40L, BAFF and FasL.

[12] The method according to [11], wherein the carrier that presents CD40L, BAFF and FasL is a feeder cell that presents CD40L, BAFF and Fast.

[13] The method according to any one of [1] to [12], wherein the B cells are human B cells.

[14] A method for producing a monoclonal antibody, comprising a step of culturing the B cell population obtained by the production method according to any one of [1] to [13] to produce a monoclonal antibody.

Advantageous Effects of Invention

According to the present invention, a B cell population comprising B cells that recognize a specific antigen can be simply and efficiently produced.

BRIEF DESCRIPTION OF DRAWINGS DESCRIPTION

FIG. 1 shows a culture schedule in the selection step of selecting a B cell population in the Examples of the present invention.

FIG. 2 shows the results obtained by subjecting a cell population after the B cell-selecting step in the Examples of the present invention to two-dimensional staining using an anti-CD19 antibody and Alexa647-labeled Her2-Tag2.

FIG. 3 shows the selection efficiency of the methods of selecting B cells in the Examples and Comparative Examples of the present invention.

EMBODIMENT OF CARRYING OUT THE INVENTION

The present invention will be described below.

The method for producing a B cell population of the present invention is a method for producing a B cell population, comprising: a step (c) of culturing a cell population comprising B cells together with a specific antigen in the absence of IL-21, in the absence of IL-4, and in the presence of a cytokine other than IL-21 and IL-4, while giving stimulation mediated by CD40 and a BAFF receptor to the cells; and a step (d) of culturing the cell population comprising B cells, while giving stimulation mediated by Fas to the cells, so as to obtain a B cell population comprising B cells that recognize the specific antigen. The B cells recognizing a specific antigen, which are produced by the method of the present invention, are preferably B cells specific to the specific antigen.

<Regarding Step (c)>

The step (c) of the present invention is a step of culturing a cell population comprising B cells together with a specific antigen in the absence of IL-21, in the absence of IL-4, and in the presence of a cytokine other than IL-21 and IL-4, while giving stimulation mediated by CD40 and a BAFF receptor to the cells.

The cell population comprising B cells used in the present invention is not particularly limited, as long as it is generally a cell population derived from peripheral blood cells, bone marrow cells, or lymphoid organs, such as, for example, splenic cells. In addition, the B cells may be either antigen-unreacted naive B cells, or memory B cells after contact with antigens. Herein, the term "naive B cells" is used in the present description to generally indicate mature B cells that have not been reacted with antigens. The naive B cells used herein correspond to CXCR5-positive and CD40-positive surface antigen-presenting cells.

Moreover, the cell population used in the present invention is not particularly limited, as long as it has CD40, a BAIT receptor (BAFF-R) and Fas, and expresses a B cell receptor (BCR) capable of recognizing an antigen. Further, the present cell population may also comprise B cells at a different stage in the differentiation process, unless it impairs the objects of the present invention. From the viewpoint of selection efficiency of culture, CD138-positive (plasma) cells, or cells other than the B cells, such as, for example, T cells, monocytes or NK cells, are preferable eliminated.

The cell population used in the present invention may be a cell population derived from an organism whose immune system has been established. Examples of the organism as an origin of the present cell population may include primates such as a human or a monkey and ungulates such as a swine, a bovine or a horse, as mammals, rodents as small mammals, such as a mouse, a rat or a rabbit, and birds such as a chicken or a quail. The origin of the present cell population is preferably a primate, and the primate may be, for example, a human. That is to say, the B cells used in the present invention are preferably human B cells. To a method of preparing a cell population from biological tissues such as spleen, conditions for preparation of an ordinary B cell population may be directly applied. In addition, the present cell population is not limited to an organism-derived, cell population, and it may also be an established B cell line.

Ordinary culture conditions, in which a medium used in the culture of B cells is used, may be generally applied to the culture of the B cell population. Examples of the medium may include Dulbecco's Modified Eagle's Medium (D-MEM) and RPMI1640. To these culture media, various types of additives applicable to ordinary cell culture, such as serum, various types of vitamins, and various types of antibiotics, may be generally added.

As culture conditions such as a culture temperature, culture conditions generally used for B cells may be directly applied. Examples of such culture conditions may include 37° C. and 5% (v/v) $CO_2$.

The seeding density, at which a cell population is seeded in a culture medium, is different depending on the origin of the cell population, the conditions of cells prepared from tissues, and the number of days in which the culture is carried out in a single culture system. The seeding density is generally $1\times10^2$ cells to $1\times10^7$ cells/cm$^2$, and preferably $1\times10^3$ cells to $1\times10^6$ cells/cm$^2$. In particular, since human. B cells have a high proliferation rate when the culture thereof is initiated at a high density, the cell density may be preferably set from 1×10⁴ cells to 1×10⁶ cells/cm². If the cell density is within this range, the cells can be prevented from being in a proliferative state, after the culture for approximately 3 days.

The B cells used in the present invention is required to have CD40, a BAFF receptor (BAFF-R) and has, so that intracellular signals are generated by the stimulation mediated by the CD40, the BAFF receptor and the has at a stage of giving stimulation to a specific antigen. The stimulation given to these molecules is not particularly limited, as long as it recognizes these molecules from the outside thereof and generates intracellular signals inside of the B cells having CD40, a BAFF receptor and has. Examples of the stimulation may include an antibody or an antibody fragment which recognizes all or a part of these molecules, a CD40 ligand (CD40L), BAFF, and a Fas ligand (FasL). Besides, the stimulation mediated by CD40 and a BAFF receptor may also have a form in which one or more of CD40L and BAFF is replaced with an antibody or an antibody fragment against CD40 or BAFF and is then given (see Patent Document 1).

CD40l is a ligand for CD40, and the amino acid sequence of CD40L has been known (see, for example, Nature, Vol. 357, pp. 80-82 (1992), and EMBO J., Vol. 11, pp. 4313-4321 (1992)). In the present invention, it is adequate if the sequence of CD40L is preserved to such an extent that the binding ability of an active domain thereof associated with receptor-binding ability is not lost. For example, if the active domain of certain CD40L shows homology of 80% or more at the amino acid sequence level with that of the original CD40L, it can be used in the present invention. Such CD40L may be isolated from naturally expressing cells, or may also be synthesized based on the known amino acid sequence. In addition, the CD40L may have a form capable of giving signals corresponding to the presence of CD40L to B cells in a culture system. The CD40L may have a free form, or a membrane-bound form.

In order to form a cell population comprising IgG-positive B cells, the stimulating factor for CD40, such as free-form CD40L, may be present in a culture system in a concentration in which B cells are able to maintain their proliferation. The concentration may be, for example, from 10 ng/mL to 10 µg/ml. Taking into consideration a relative decrease in the concentration attended with proliferation of B cells, the concentration can be set from 50 ng/mL to 10 µg/ml.

BAFF (B cell activation factor: B cell activation factor belonging to the tumor necrosis factor family) is a TNF analog molecule that has been known to be associated with proliferation and differentiation of B cells that have reacted with antigens. The amino acid sequence of BAFF has already been known (for example, J Exp Med, Vol. 189, pp. 1747-1756 (1999), Science, Vol. 285, pp. 260-263 (1999), and J Bio Chem, Vol. 274, pp. 15978-15981, (1999)). In the present invention, it is adequate if the sequence of BAFF is preserved to such an extent that the binding ability of an active domain thereof associated with receptor-binding ability is not lost. For example, if the active domain of certain BAFF shows homology of 80% or more at the amino acid sequence level with that of the original. BAFF, it can be used in the present invention. Such BAFF may be isolated from naturally expressing cells, or may also be synthesized based on the known amino acid sequence. In addition, the BAFF may have a form capable of giving signals corresponding to the presence of BAFF to IgG-positive B cells in a culture system. The BAFF may have a free form (i.e., secretory form), or a membrane-bound form.

In order to form a cell population comprising IgG-positive B cells, the stimulating factor for BAFF receptor, such as free-form BAFF, may be present in a culture system in a concentration in which B cells are able to maintain their proliferation. Such a concentration may be, for example, from 10 ng/mL to 10 µg/ml. From the viewpoint that a higher survival supporting activity can be expected if the stimulating factor for BAFF receptor is present at a higher concentration, the concentration can be preferably set from 50 ng/mL to 10 µg/ml.

As in the case of the above-mentioned cell population, examples of the origins of CD40L and BAFF may include primates and ungulates as mammals, rodents as small mammals, and birds. The CD40L and BAFF are preferably derived from rodents and mammals, and examples of such rodents and mammals may include mice and humans. In addition, the CD40L and BAFF may be derived either from the same species as that of the above-described cell population as a presentation target, or from species different from that of the above-described cell population.

An antibody or an antibody fragment against CD40 or a BAFF receptor can be obtained according to a method known in the present technical field. The type of such an antibody is not particularly limited, as long as it is an antibody having an ability to bind to CD40 or a BAFF receptor.

Such an antibody or an antibody fragment may have a form, in which it is presented on the surface of a carrier, or may also have a free form or a solubilized form, in which it is not immobilized on the surface of the carrier.

In the step (c), the cell population comprising B cells are cultured together with a specific antigen in the absence of IL-21, in the absence of IL-4, and in the presence of a cytokine other than IL-21 and IL-4.

As such a cytokine other than IL-21 and IL-4, a B cell activation factor (any given, various types of cytokines or growth factors known to activate and/or induce differentiation of B cells) can be used. Specifically, the type of the B cell activation factor is not particularly limited, but examples may include interleukin (which includes, so far, interleukin subfamily such as IL-1 to IL-38 and IL-17B to IL-17D, OSM (oncostatin M), LIF (leukocyte migration inhibitory factor), CNTF (ciliary neurotrophic factor), and CT-1), IFN-α, IFN-β, IFN-γ, C type chemokine XCL1 and XCL2, C-C type chemokine (which includes, so far, CCL1 to CCL28), CXC-type chemokine (which includes, so far, CXCL1 to CXCL17), TNF superfamily members (which include, so far, TNESF1 to TNFSF18), Toll-like receptor agonists (including LPS and CpG), TGF-β superfamily (including TGF-β and activin), and cell growth factors (including those transmitting signals through receptor tyrosine kinase, such as SCF, Flt3 ligand, M-CSF, GM-CSF, or insulin). Among the above-described B cell activation factors, those whose receptors are expressed on the surface of the B cells can be used.

The cytokine other than IL-21 and IL-4 is preferably an interleukin other than IL-21 and IL-4.

The cytokine other than IL-21 and IL-4 is preferably at least one type of cytokine selected from IL-2, the IL-10 family and the IL-12 family.

The cytokine belonging to the IL-10 family and the IL-12 family may be derived from a naturally occurring cytokine, or may also be a biotechnologically obtained recombinant cytokine. As in the case of the above-mentioned cell population, examples of the origin of the cytokine belonging to the IL-10 family and the IL-12 family may include primates and ungulates as mammals, rodents as small mammals, and birds. These molecules are preferably each derived from rodents and mammals, and examples of such rodents and mammals may include mice and humans. In addition, they may be cells derived from the same species as that of the above-described cell population as a presentation target, or may also be cells derived from species different from that of the above-described cell population.

The IL-10 cytokine family includes IL-10, IL-19, IL-20, IL-24, and IL-26. Although the action mechanism of the IL-10 cytokine family on B cells has not yet been entirely elucidated, it has been reported that the IL-10 cytokine family suppresses differentiation of the B cells (Non-Patent Document: Blood, 115(9): 1718-26 (2010)).

The IL-12 cytokine family includes IL-12, IL-23, IL-27, IL-30, and IL-35. Although the action mechanism of the IL-12 cytokine family on B cells has not yet been entirely elucidated, it has been repotted that the IL-12 cytokine family activates human B cells via the signal transduction and transcriptional activation factors STAT1 and STAT3 (Non-Patent Document: Journal of Immunology, 176(10): 5890-7 (2006)).

A specific example of the cytokine other than IL-21 and IL-4 may be at least one type selected from IL-2, IL-20, IL-24 and IL-27.

The concentration of the cytokine other than IL-21 and IL-4 cytokines belonging to the IL-10 family or the IL-12 family, etc.) is not particularly limited, as long as it is a concentration in which B cells having an affinity for the specific antigen are able to proliferate. In general, the concentration of the cytokine other than IL-21 and IL-4 is set at preferably 10 ng/mL to 1 µg/mL, and more preferably 10 ng/mL to 100 ng/mL.

Moreover, when the cytokine other than IL-21 and IL-4 is IL-2, the concentration thereof is set at preferably 1 unit/mL to 1000 units/mL, and more preferably 10 units/mL to 500 units/mL.

One unit of IL-2 is defined with the specific activity unit/mg) of cytokine, and this is a unit applied only when the reaction volume curve of cytokine is a sigmoid curve. The specific activity is calculated according to the following equation:

Specific activity (unit/mg)=$1 \times 10^6 / ED_{50}$ (ng/mL).

Accordingly, the specific activity depends on $ED_{50}$ (ng/mL). $ED_{50}$ (ng/mL) is defined as a cytokine concentration causing 50% of the maximum response, and in general, $ED_{50}$ (ng/mL) is determined by the results of a standardized bioassay. In the case of IL-2, $ED_{50}$ (ng/mL) calculated according to the mouse CTLL-2 assay is adopted.

In the step (c), the cell population comprising B cells is cultured together with a specific antigen.

In the step (c), the specific antigen presented to B cells means an antigen, for which the B cells exhibit an affinity, and the specific antigen is appropriately selected depending on purpose. The type of the antigen is not particularly limited, as long as it exhibits antigenicity, and examples of such an antigen may include nucleic acids such as DNA or RNA, a sugar chain, a lipid, an amino acid, a peptide, a protein, a hapten, and a low-molecular-weight compound. These substances may be presented in a form in which B cells are able to recognize the substances, and such a form may be either a free form or a carrier-immobilized form. From the viewpoint of reliable presentation of the antigen to B cells, the antigen is preferably in a form in which it is immobilized on a carrier.

In order to enhance the antigen recognition properties of B cells, in addition to a form in which the antigen alone is used, the antigen may also have forms known in the present technical field, such as a form in which a known auxiliary molecule is added to the antigen, or a form in which the antigen binds to an antibody molecule.

When such a binding form to an antibody molecule or a fusion protein consisting of a protein antigen and an antibody F region is applied to antigen presentation, an anchorage for presenting an antigen on the surface of a carrier, for example, an Fc receptor molecule, protein A, protein G, or protein L, may be further used.

In addition, a fusion protein consisting of a protein binding to a constituent of a carrier and an antigen protein may also be used. Moreover, when a membrane-type protein is presented as an antigen, the gene of the protein may be introduced using an expression vector into a cell used as a carrier, and it may be then expressed therein. In the case of other proteins, they may be introduced into a cell used as a carrier, using an expression vector capable of expressing a fusion protein consisting of a suitable signal peptide (which is not necessary in the case of a secretory protein) and a suitable transmembrane region (e.g. a region of MHC class I), and may be then expressed therein.

In the step (c), it is preferred that the cell population comprising B cells is cultured using a carrier that presents CD40L, BAFF and a specific antigen.

From the viewpoint of reliably giving intracellular signals to B cells in the culture system, CD40L and BAFF are preferably in a form in which they are presented on the surface of the carrier.

Examples of the carrier used to present each molecule on the surface may include, but are not particularly limited to, carries commonly used to present the above-described molecule on the surface, including a cell, an artificial lipid bilayer, a plastic such as polystyrene or polyethylene terephthalate, collagen, nylon, a polysaccharide such as nitrocellulose, agar, agarose or sepharose, a paper, and a glass. The shape of such a carrier is not particularly limited, and all shapes such as a sheeted, planar, spherical, spongy, or fibrous shape, may be adopted. From the viewpoint of reliable selectivity of cells, the carrier is preferably a cell. Examples of the cell that can be used as a carrier may include fibroblasts (e.g., 3T3 cells, L cells, etc.), epithelial cells (e.g., HeLa cells), embryonic kidney cells (e.g., HEK293 cells, etc.), and follicular dendritic cells. From the viewpoint of high proliferation rate, large cell surface area, and easy removal of feeder cells, fibroblasts are preferable among these cells.

The carrier that presents CD40L, BAFF and a specific antigen is preferably a feeder cell that presents CD40L, BAH and a specific antigen.

The feeder cell that presents CD40L, BAFF and a specific antigen on the surface thereof can be produced by a person skilled in the art according to a genetic recombination technique or the like, based on the known sequences of CD40L, BAFF, and the specific antigen.

As in the case of the aforementioned cell population, examples of the origin of the feeder cell may include primates and ungulates as mammals, rodents as small mammals, and birds. Preferred examples may include rodents and mammals, such as mice and humans. Moreover, such feeder cells may be either cells derived from the same species as the above-described cell population as a presentation target, or cells derived from species different from that of the above-described cell population.

It is to be noted that CD40L, BAFF, and a specific antigen may not be necessarily present on a single feeder cell, if they allow B cells to generate intracellular signals.

<Regarding Step (d)>

The step (d) of the present invention is a step of culturing the cell population comprising B cells, while giving stimulation mediated by Fas to the cells, so as to obtain a B cell population comprising B cells that recognize the specific antigen.

The stimulation mediated by Fas can be given by a Fas ligand (FasL). The stimulation mediated by Fas may also have the form of giving an antibody or an antibody fragment against Fas (see Patent Document 1).

The Fas ligand (FasL) is a death factor belonging to the TNF family, namely, a cytokine exhibiting an apoptosis-inducing activity. The amino acid sequence of the Fas ligand has been known (see, for example, Cell, Vol. 75, pp. 1169-1178 (1993)). In the present invention, it is adequate if the sequence of FasL, is preserved to such an extent that the binding ability of an active domain thereof associated with receptor-binding ability is not lost. For example, if the active domain of certain FasL shows homology of 80% or more at the amino acid sequence level with that of the original FasL, it can be used in the present invention. Such FasL may be isolated from naturally expressing cells, or may also be synthesized based on the known amino acid sequence. In addition, the FasL may have a form capable of giving signals corresponding to the presence of Fas to IgG-positive B cells in a culture system. The FasL may have a free form, or a membrane-bound form.

FasL may be generally present in a culture system in a concentration capable of inducing apoptosis to B cells, and such a concentration is, for example, 10 ng/mL to 10 µg/mL. In addition, from the viewpoint of inducing suppression of cell death by antigenic stimulation, the concentration can be preferably set from 10 ng/mL to 1 µg/ml.

As in the case of the above-mentioned cell population, examples of the origin of FasL may include primates and ungulates as mammals, rodents as small mammals, and birds. Fast, is preferably derived from rodents and mammals, and examples of such rodents and mammals may include mice and humans. In addition, FasL may be derived either from the same species as that of the above-described cell population as a presentation target, or from species different from that of the above-described cell population.

An antibody or an antibody fragment against Fas can be obtained according to a method previously known in the present technical field. The type of such an antibody is not particularly limited, as long as it is an antibody having a binding ability to Fas.

Such an antibody or an antibody fragment may have a form, in which it is presented on the surface of a carrier, or may also have a free form or a solubilized form, in which it is not immobilized on the surface of the carrier.

In the step (d), the cell population comprising B cells can preferably be cultured in the presence of IL-21 or in the presence of IL-21 and IL-2, while giving stimulation mediated by Fas to the cells. Moreover, the step (d) is preferably carried out in the absence of the specific antigen.

In the step (d), when IL-21 is allowed to be present, in general, the concentration of IL-21 is set preferably 1 ng/mL to 1000 ng/mL, and more preferably 1 ng/mL to 100 ng/mL.

In the step (d), when IL-2 is allowed to be present, the concentration of IL-2 is set at preferably 1 unit/nit, to 1000 units/mL, and more preferably 10 units/mL to 500 units/mL.

In the step (d), the cell population comprising B cells is preferably cultured using a carrier that presents CD40L, BAFF and FasL. That is to say, from the viewpoint of reliably giving intracellular signals to B cells in the culture system, CD40L, BAFF or FasL is preferably in a form in which they are presented on the surface of the carrier. Examples of the carrier used to present each molecule on the surface are the same as those described above in the present description.

The carrier that presents CD40L, BAFF and FasL is particularly preferably a feeder cell that presents CD40L, BAFF and FasL. The feeder cell that presents CD40L, BAH and FasL on the surface thereof can be produced by a person skilled in the art according to a genetic recombination technique or the like, based on the known sequences of CD40L, BAFF, and FasL.

As in the case of the aforementioned cell population, examples of the origin of the feeder cell may include primates and ungulates as mammals, rodents as small mammals, and birds. Preferred examples may include rodents and mammals, such as mice and humans. Moreover, such feeder cells may be either cells derived from the same species as the above-described cell population as a presentation target, or cells derived from species different from that of the above-described cell population.

It is to be noted that CD40L, BAIT, and Fas may not be necessarily present on a single feeder cell, if they allow B cells to generate intracellular signals.

<Selection Step Comprising Step (c) and Step (d)>

A step comprising the above-described step (c) and step (d) is also referred to as a "selection step." Although it depends on conditions such as seeding density and cell type, the selection step is generally carried out for one day or more after initiation of the selection step, from the viewpoint of performing reliable selection. The selection step may also be carried out for 1 to 3 days, and preferably for 1 to 2 days, from the viewpoint of performing reliable selection. The time required for the selection step may also be longer, if the viability of cells can be maintained, and thus, antigen-specific B cells having a higher affinity for a specific antigen can be obtained by culturing the cells for a longer period of time.

Moreover, in order to improve the affinity of B cells for an antigen, the selection step may be repeatedly carried out, while replenishing feeder cells. At that time, in order to improve the affinity of the B cells for an antigen, it may also be possible to change (decrease) the concentration or valence of the antigen, every time the step is repeated. Furthermore, in order to improve the affinity of the B cells for an antigen, it may further be possible to add a culture supernatant obtained from the immediately previous step or an antibody generated in the culture supernatant to the culture system, when the subsequent step is carried out. Thereby, a competition is generated between the B cell receptor and the antibody, so that B cells having a higher-affinity B cell receptor can be selected.

<Regarding Step (a) and Step (b)>

In the present invention, before the step (c), a step (a) of culturing the cell population comprising B cells in the presence of IL-4 or in the presence of IL-4 and IL-2, while giving stimulation mediated by CD40 and a BAFF receptor to the cells, may also be established.

In the present invention, between the step (a) and the step (c), a step (b) of culturing the cell population comprising B cells in the presence of IL-21 or in the presence of IL-21 and IL-2, while giving stimulation mediated by CD40 and a BAFF receptor to the cells, may further be established.

The operation of giving the stimulation mediated by CD40 and a BAFF receptor to the cells in the step (a) and the step (b) can be carried out by the same method as that described above in the present description.

In the case of performing the step (a), the culture period is not particularly limited. It is generally for 1 to 14 days, and preferably for 3 to 10 days.

In the case of performing the step (b), the culture period is not particularly limited. It is generally for 1 to 7 days, and preferably for 2 to 4 days.

In general, the concentration of IL-4 in the step (a) is set at preferably 1 ng/mL to 1 μg/mL, and more preferably 10 ng/mL to 100 ng/mL.

The concentration of IL-2 in the step (a) is set at preferably 1 unit/mL to 1000 units/mL, and more preferably 10 units/mL to 500 units/mL.

In general, the concentration of IL-21 in the step (b) is set at preferably 1 ng/mL to 1000 ng/mL, and more preferably 1 ng/mL to 100 ng/mL.

The concentration of IL-2 in the step (b) is set at preferably 1 unit/mL 1000 units/mL, and more preferably 10 units/mL to 500 units/mL.

<B Cell Population Comprising B Cells that Recognize a Specific Antigen>

According to the above-described method of the present invention, the B cell population comprising B cells that recognize a specific antigen is produced. The above-described B cell population comprising B cells that recognize a specific antigen is preferably an "antigen-specific B cell population." The "antigen-specific B cell population" is used herein to collectively mean the obtained cells, and the meaning of the term is not limited by the number of cells. That is to say, this term is also used to indicate a case where there is only a single cell, as well as a case where there are a plurality of cells.

It is preferable that the B cell population comprising B cells that recognize a specific antigen, which is produced by the method of the present invention, be mainly composed of B cells having specificity to the used specific antigen. Such an antigen-specific B cell population comprises a higher density of B cells having specificity to the antigen, for example, than a B cell population present in peripheral blood from a living body primarily contacted with the same antigen as described above.

Accordingly, the antigen-specific B cell population produced by the method of the present invention can be preferably used in the production of a monoclonal antibody, cell therapy, and the like, which require large quantities of B cells having an affinity for the specific antigen.

<Method for Producing Monoclonal Antibody>

According to the present invention, provided is a method for producing a monoclonal antibody, comprising a step of culturing the B cell population obtained by the above-described method of the present invention to produce a monoclonal antibody. Thereby, a monoclonal antibody against a specific antigen can be simply and promptly obtained.

In the method for producing a monoclonal antibody according to the present invention, a publicly known method for producing hybridomas may be applied to the above-described B cell population. Specifically, according to a publicly known cell fusion method, myeloma cells or the like may be applied to the cell population comprising IgG-positive B cells obtained by the present invention, so as to obtain hybridomas. Thereafter, from the obtained hybridomas, hybridomas producing antibodies of interest may be isolated by a limiting dilution method or the like, and antibodies produced from the isolated hybridomas may be then recovered. Alternatively, a method which comprises isolating an antibody gene from the above-described antigen-specific B cell population, and then producing a monoclonal antibody according to genetic recombination, may also be applied.

The present invention will be described in the following examples. However, these examples are not intended to limit the scope of the present invention.

Examples (1) Culture of Cells

B cells were cultured in RPMI-1640 (supplemented with 10% (v/v) FCS (fetal bovine serum), penicillin/streptomycin, 2 mM L-glutamine, 55 nM 2-mercaptoethanol, 10 mM HEPES, and 1 mM sodium pyruvate) that was used as a medium for the culture of B cells, under conditions of 5% (v/v) $CO_2$ and 37° C., unless otherwise particularly specified.

Feeder cells presenting CD40L and BAIL on the surface thereof, which were used upon the culture of B cells, namely, 40LB cells, were cultured in D-MEM (supplemented with 10% (v/v) FCS and penicillin/streptomycin) used as a medium for the culture of 40LB cells, under conditions of 5% (v/v) $CO_2$ and 37° C., unless otherwise particularly specified.

Upon the experiment of the culture of B cells, 40LB cells were seeded in a cell count of $2.7 \times 10^6$ cells on a cell culture plate with a diameter of 99 mm (manufactured by Sumitomo Bakelite Co., Ltd.), and were then cultured for 24 hours to form a monolayer. Thereafter, the monolayer was irradiated with an X-ray (120 Gy) and was then used.

(2) Preparation of Feeder Cells

In order to carry out the FAIS (Las-mediated Antigen-specific iGB-cell Selection) method (PLoS One, 19; 9(3): e92732.2014)) to select an antigen-specific B cell population, 40LB-Her2 and 40LB-FasL cells were used.

For the 40LB-Her2 cells, human Her2 was introduced into 40 cells using a lentiviral vector according to a common method, so that it was allowed to be constantly expressed, thereby producing clones.

For the 40LB-FasL cells, as with the description of Patent Document 1, mouse FasL was introduced into 40LB cells using a lentiviral vector according to a common method, so that it was allowed to be constantly expressed, thereby producing clones.

(3) Preparation of Human B Cells

Monocytes were separated from the peripheral blood of a healthy human subject, using Lymphoprep Tube (manufactured by AXIS SHIELD), and were then subjected to FcR Blocking Reagent (manufactured by Miltenyi Biotec). Thereafter, using biotin-anti-human CD2 antibody (manufactured by Biolegend), biotin-anti-human CD235a antibody (manufactured by eBioscience), and Streptavidin-Particle Plus-DM (manufactured by BD Pharmingen), CD2-negative cells and CD235a-negative cells were recovered by employing RD iMag Cell Separation Magnet (manufactured by BD Bioscience) and MACS Separation Columns (manufactured by Miltenyi Biotec). Among the recovered cells, CD19-positive cells were recovered using PE-anti-human CD19 antibody (manufactured by Biolegend), and employing: a cell sorter (BD FACS AriaIII).

The thus prepared B cells were cultured in accordance with the schedule shown in FIG. 1.

(4) Preparation of Antigen-Specific B Cell Receptor-Expressing B Cell Population A B cell population comprising antigen-specific B cells was obtained as follows. Specifically, CSIV-CMV-MCS-IRES2-Venus Vector (Cancer Science, Vol. 105, pp. 402-408

(2014)) was recombined, so as to produce CSIV-CMV-mGK (Herceptin kappa-Light chain)—IRES2—mGH (Herceptin Heavy chain), into which the heavy chain and light chain of a Her2 antigen-specific B cell receptor (Herceptin antigen gene) was incorporated, thereby constructing a Herceptin expression vector. Using this expression lentiviral vector, a Her2 antigen-specific B cell receptor was allowed to express in the recovered CD19-positive B cells according to a common method, so as to obtain a B cell population expressing the Her2 antigen-specific B cell receptor.

(5) Preparation of Human B Cells (Culture Step)

The above-obtained population comprising antigen-specific B cells was subjected to a primary culture for 7 days on 40LB cells, in which a monolayer was formed. Upon the culture, a B cell medium containing human IL-4 (50 ng/mL, manufactured by PEPROTECH) and human IL-2 (50 units nit, manufactured by PEPROTECH) was used, and the cells were cultured in a $CO_2$ incubator at a cell density of $1\times10^5$ cells/cm$^2$ (i.e., the step (a) described in the present description).

On Day 7 of the culture, the cells as a whole were recovered together with the feeder cells, using D-PBS containing 2 mM EDTA and 0.5% by mass of BSA. Using. Biotin-anti-mouse H-2K$^d$ antibody (manufactured by Biolegend), Biotin-anti-human CD138 antibody, and Streptavidin-Particle Plus-DM (manufactured by RD Pharmingen), the feeder cells and the antibody-producing cells were removed from the recovered B cell culture, by employing BD iMag Cell Separation Magnet (manufactured by BD Bioscience) and MACS Separation Columns (manufactured by Miltenyi Biotec). The B cells, from which the feeder cells had been removed, were seeded at a cell density of $5\times10^4$ cells/cm$^2$ or less on a newly prepared 90-mm dish, on which 40LB cells had been seeded, using a B cell medium supplemented with human IL-21 (10 ng/mL, manufactured by PEPROTECH) and human 1T-2 (50 units/mL, manufactured by PEPROTECU), and were then cultured (i.e., the step (b) described in the present description).

(6) Selective Culture of Antigen-Specific B Cells (Selection Step)

On Day 10 of the culture, in order to perform selective culture for Her2 antigen-specific B cells, the feeder cells and the antibody-producing cells were removed from the recovered B cell culture in the same manner as that described in the above (5). The B cells, from which the feeder cells had been removed, were seeded at a cell density of $2\times10^5$ cells/cm$^2$ on a newly prepared 90-mm dish, on which 40LB cells had been seeded, using a B cell medium supplemented with human IL-2 (50 units/mL, manufactured by PEPROTECH), and a culture before antigenic stimulation was then performed. At that time, the following conditions were applied regarding cytokines present in the B cell medium: addition of only human IL-2; addition of cytokine families that stimulate receptors having a common chain, namely, human IL-4 (50 ng/mL, manufactured by PEPROTECH) and human IL-21 (50 ng/mL, manufactured by PEPROTECH), as well as human IL-2; addition of the IL-10 cytokine families, namely, human IL-20 (50 ng/mL, manufactured by PEPROTECH) and human IL-24 (100 ng/mL, manufactured by PEPROTECH), as well as human IL-2; and addition of the IL-12 cytokine family, human IL-27 (50 ng/mL, manufactured by R & D Systems), as well as human IL-2.

Forty-eight hours later (i.e., Day 12 of the culture), using Biotin-anti-mouse H-2K$^d$ antibody (manufactured by Biolegend), Biotin-anti-human CD138 antibody; and Streptavidin-Particle Plus-DM (manufactured by BD Pharmingen), the feeder cells and the antibody-producing cells were removed from the whole cells. The B cell population, from which the feeder cells and the antibody-producing cells had been removed, and which had been subjected to a culture before antigenic stimulation, were continuously suspended in a B cell medium containing cytokine(s) under the same conditions as those described above, and were then cultured together with 40LB-Her2 cells forming a monolayer, so that antigenic stimulation was given to antigen-specific B cells (i.e., the step (c) described in the present description).

Forty-eight hours later (i.e., Day 14 of the culture), the feeder cells and the antibody-producing cells were removed from the whole cells by the same method as that described above. The B cell population under individual conditions, from which the 40LB-Her2 cells and the antibody-producing cells had been removed, and which had been subjected to a antigenic stimulation culture, were suspended in a B cell medium containing human IL-21 (10 ng/mL, manufactured by PEPROTECH) and human IL-2 (50 units/mL, manufactured by PEPROTECH), and were then cultured together with 40LB-FasL, cells forming a monolayer, so that cell death stimulation was given to the cultured B cell population as a whole (i.e., the step (d) described in the present description).

Twenty-four hours later (i.e., Day 15 of the culture), using Biotin-anti-mouse H-2K$^d$ antibody (manufactured by Biolegend), Biotin-anti-human CD178 (FasL) antibody (manufactured by Biolegend), and Streptavidin-Particle Plus-DM (manufactured by BD Pharmingen), the 40LB-FasL cells were removed from the whole cells, by employing BD iMag Cell Separation Magnet (manufactured by BD Bioscience) and MACS Separation Columns (manufactured by Miltenyi Biotec), Using ClioCell Pro Kit (manufactured by ClioCell), dead cells were further removed from the B cell population, from which the 40LB-FasL cells had been removed. Thereafter, the B cell population, from which the feeder cells and the dead cells had been removed, was suspended in a B cell medium containing human IL-21 (10 ng/mL, manufactured by PEPROTECH) and human IL-2 (50 units/mL, manufactured by PEPROTECH), and was then subjected to a recovery culture on novel 40LB cells.

After completion of the cell death stimulation, the recovery culture was carried out for 6 days. The thus cultured cells were recovered, and then, using FITC-anti-mouse H-2K$^d$ antibody (manufactured by Biolegend), PE-anti-human CD19 antibody (manufactured by Biolegend), and Alexa647-labeled Her2-Tag2 protein, Her2 antigen-specific B cells were detected by employing a flow cytometer (BD FACS AriaIII). The results are shown in FIG. 2.

The numerical value shown in the figure indicates the percentage (%) of cells contained in each region.

Based on the percentage of the cells without selection and the percentage of the cells with selection, as shown in FIG. 2, the selection efficiency (-fold) of selective culture is shown in FIG. 3.

As shown in FIG. 3, it was confirmed that when the cytokine conditions applied in the selection step were changed to the absence of IL-21 described in Patent Document 1, or to the IL-10 cytokine family or the IL-12 cytokine family, the efficiency of selecting antigen-specific B cells is improved.

The invention claimed is:

1. A method for producing a B cell population, comprising:
   a step (c) of culturing a cell population comprising B cells together with a specific antigen in the absence of IL-21, in the absence of IL-4, and in the presence of a cytokine other than IL-21 and IL-4, while giving stimulation mediated by CD40 and a BAFF receptor to the cells; and a step (d) of culturing the cell population comprising B cells, while giving stimulation mediated by Fas to the cells, so as to obtain a B cell population comprising B cells that recognize the specific antigen.

2. The method according to claim 1, wherein the cytokine is an interleukin other than IL-21 and IL-4.

3. The method according to claim 1, wherein the cytokine is at least one type of cytokine selected from the group consisting of IL-2, the IL-10 family and the IL-12 family.

4. The method according to claim 1, wherein the cytokine is at least one type selected from the group consisting of IL-2, IL-20, IL-24 and IL-27.

5. The method according to claim 1, wherein, in the step (d), the cell population comprising B cells is cultured in the presence of IL-21 or in the presence of IL-21 and IL-2, while giving stimulation mediated by Fas to the cells.

6. The method according to claim 1, wherein the step (d) is carried out in the absence of the specific antigen.

7. The method according to claim 1, further comprising, before the step (c), a step (a) of culturing a cell population comprising B cells in the presence of IL-4 or in the presence of IL-4 and IL-2, while giving stimulation mediated by CD40 and a BAFF receptor to the cells.

8. The method according to claim 7, further comprising, between the step (a) and the step (c), a step (b) of culturing the cell population comprising B cells in the presence of IL-21 or in the presence of IL-21 and IL-2, while giving stimulation mediated by CD40 and a BAFF receptor to the cells.

9. The method according to claim 1, wherein the step (c) is a step of culturing the cell population comprising B cells, using a carrier that presents CD40L, BAFF and a specific antigen.

10. The method according to claim 9, wherein the carrier that presents CD40L, BAFF and a specific antigen is a feeder cell that presents CD40L, BAFF and a specific antigen.

11. The method according to claim 1, wherein the step (d) is a step of culturing the cell population comprising B cells, using a carrier that presents CD40L, BAFF and FasL, while giving stimulation mediated by CD40, a BAFF receptor and Fas to the cells.

12. The method according to claim 11, wherein the carrier that presents CD40L, BAFF and FasL is a feeder cell that presents CD40L, BAFF and FasL.

13. The method according to claim 1, wherein the B cells are human B cells.

* * * * *